United States Patent [19]
Bateson

[11] Patent Number: 5,627,075
[45] Date of Patent: May 6, 1997

[54] STABLE DIAGNOSTIC REAGENT

[75] Inventor: Joseph E. Bateson, Carmel, Ind.

[73] Assignee: Boehringer Mannheim Corporation, Indianapolis, Ind.

[21] Appl. No.: 619,118

[22] Filed: Mar. 20, 1996

Related U.S. Application Data

[63] Continuation of Ser. No. 80,263, Jun. 21, 1993, abandoned.

[51] Int. Cl.$^6$ .................................................. G01N 31/00
[52] U.S. Cl. .................. 436/8; 436/14; 436/95; 436/176; 435/14; 435/28
[58] Field of Search ........................... 436/8, 14, 18, 436/95, 176; 435/14, 28

[56] References Cited

U.S. PATENT DOCUMENTS

| | | | |
|---|---|---|---|
| 3,886,045 | 5/1975 | Meiattini | 195/103.5 |
| 4,189,536 | 2/1980 | Green | 435/12 |
| 4,229,369 | 10/1980 | Green | 260/501.19 |
| 4,384,042 | 5/1983 | Miike et al. | 435/25 |
| 4,529,525 | 7/1985 | Dormal et al. | 252/132 |
| 4,532,064 | 7/1985 | Boskamp | 252/105 |
| 4,781,890 | 11/1988 | Arai et al. | 422/56 |
| 4,900,475 | 2/1990 | Ramachandran et al. | 252/532 |
| 4,916,058 | 4/1990 | Aoyama et al. | 435/10 |
| 5,116,729 | 5/1992 | Ismail et al. | 435/14 |
| 5,185,247 | 2/1993 | Ismail et al. | 435/14 |

FOREIGN PATENT DOCUMENTS

| | | | |
|---|---|---|---|
| 0072581B1 | 4/1987 | European Pat. Off. | C12Q 1/00 |
| 0386562A2 | 9/1990 | European Pat. Off. | C12Q 1/26 |
| 57-138389 | 8/1982 | Japan | C12N 9/96 |
| 63-202381 | 8/1988 | Japan | C12N 9/96 |
| WO86/04610 | 8/1986 | WIPO | C12Q 1/00 |

*Primary Examiner*—David A. Redding
*Attorney, Agent, or Firm*—Barnes & Thornburg

[57] ABSTRACT

The inclusion of succinic acid or a salt thereof to stabilize compositions that include glucose oxidase and/or ferricyanide. Typically, the succinic acid or succinic acid salt is included in a diagnostic reagent utilized in test strips or test solutions useful for the analysis of glucose from a fluid sample.

20 Claims, 2 Drawing Sheets

5,627,075

STABLE DIAGNOSTIC REAGENT

This application is a continuation of U.S. patent application Ser. No. 08/080,262, filed Jun. 21, 1993, now abandoned.

FIELD OF THE INVENTION

This invention relates to the stabilization of compositions that include glucose oxidase and/or ferricyanide.

BACKGROUND OF THE INVENTION

Compositions, such as diagnostic reagent compositions, that include glucose oxidase or ferricyanide have poor stability due to the tendency for glucose oxidase and ferricyanide to degrade.

Succinic acid and some salts of succinic acid have been used in the following references as a stabilizing agent (stabilizing, for example, a detergent composition) or a chelating agent:

Boskamp, U.S. Pat. No. 4,532,064, issued Jul. 30, 1984;

Thomas, International Patent Application Publication No. WO 86/04610, published Aug. 14, 1986;

Ramachandran et al., U.S. Pat. No. 4,900,475, issued Feb. 13, 1990;

Dormal et al., U.S. Pat. No. 4,529,525, issued Jul. 16, 1985;

Denney, European Pat. Specification EPO 072 581 B1, issued Apr. 8, 1987; JP 63202381, published Aug. 22, 1988; and JP 57138389, published Aug. 26, 1982.

None of these references discloses the use of succinic acid or a salt thereof to stabilize an aqueous or dried reagent that includes glucose oxidase and/or ferricyanide.

SUMMARY OF THE INVENTION

The invention is a stable composition of matter useful as a diagnostic reagent for the analysis of glucose from a fluid sample and a process for stabilizing compositions that include glucose oxidase and/or ferricyanide.

The invention is based upon the surprising result that the inclusion of succinic acid or a salt thereof will stabilize a composition that includes glucose oxidase and/or ferricyanide.

Preferably, the succinic acid or a salt thereof is disodium succinate, which is utilized in a diagnostic reagent useful for the analysis of glucose in a biosensor. The reagent is preferably made up in an aqueous slurry that includes glucose oxidase, potassium phosphate (buffer), potassium ferricyanide (a redox mediator), a dispersant and crystallization inhibitor, such as AVICEL RC-591F, which is a blend of 88% microcrystalline cellulose and 12% sodium carboxymethylcellulose, a small amount of hydroxyethylcellulose, a surfactant (such as TRITON X-100 surfactant, which includes various polyoxyethylene ethers), and water. After mixing, the resulting slurry may be coated onto the surface of working and counter electrodes in an electrochemical biosensor, dried, and subsequently utilized in the measurement of glucose from a fluid sample, as described herein.

More broadly, succinic acid or a salt thereof may stabilize other compositions of matter that include either glucose oxidase and/or ferricyanide, such as various kinds of glucose test reagents that utilize either glucose oxidase and/or ferricyanide.

DESCRIPTION OF THE INVENTION

Figure 1:
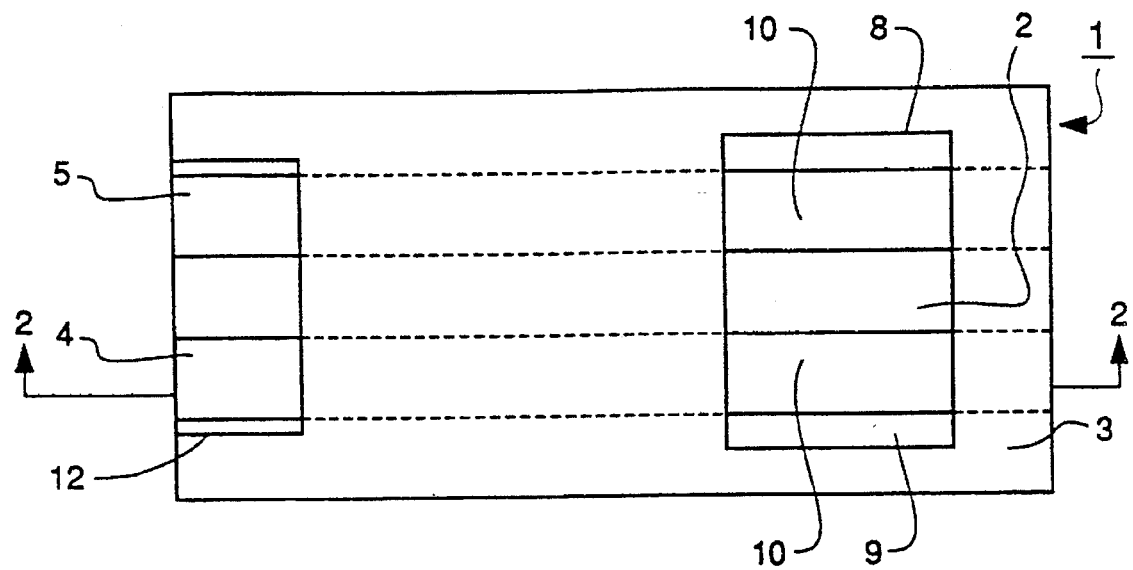
FIG. 1 is a schematic top view of a biosensor which may utilize the stable composition of the present invention.

A specific embodiment of the present invention will first be described. This specific embodiment utilizes a reagent that has been made more stable by the inclusion of disodium succinate. A protocol for making the reagent is as follows:

Step 1— Prepare 1 liter (in a volumetric flask) of a buffer/NATROSOL mixture by adding 1.2 grams (g) hydroxyethylcellulose (sold under the mark NATROSOL 250 M NF, available from Aqualon Company) to 0.74 molar (M) aqueous potassium phosphate and 26.4 g dibasic potassium phosphate at pH 6.25. Allow the buffer/NATROSOL mixture to stir and swell for 3 hours.

Step 2— Prepare an AVICEL mixture by stirring 14 g AVICEL RC-591F dispersant and crystallization inhibitor (available from FMC Corporation) and 504.8 g water for 20 minutes.

Step 3— Prepare a TRITON mixture by adding 0.5 g TRITON X-100 surfactant to 514.6 g of the buffer/NATROSOL mixture and stir for 15 minutes.

Step 4— While stirring, add the total TRITON mixture dropwise with a dropwise addition funnel or buret to the total AVICEL mixture. Once addition is complete, continue stirring overnight.

Step 5— To the mixture resulting from Step 4, add, while stirring, 98.8 g potassium ferricyanide. (Add a little potassium ferricyanide at a time to allow the potassium ferricyanide to dissolve as added.)

Step 6— Stir the resulting mixture of Step 5 for 20 minutes.

Step 7— Adjust the pH of the mixture resulting from Step 6 to 6.25 by adding potassium hydroxide.

Step 8— To the resulting mixture of Step 7, add 9.2 g glucose oxidase (218.5 ortho-dianisidine units per milligram (mg) from Biozyme) and stir at least 20 minutes.

Step 9— To the resulting mixture of Step 8, add 10 g (37 millimoles (mmol)) disodium succinate hexahydrate and stir at least 20 minutes.

Step 10— Filter the resulting mixture of Step 9 through a 100 micron sieve bag to remove any AVICEL clumping. The filtrate is the resulting reagent composition 11 (see FIG. 2), which is added to the electrode surfaces of the electrochemical biosensor, described below, and is then dried. (Before drying, this composition is 0.37 molar in phosphate buffer. A more preferred formulation is made 0.25 molar in phosphate buffer. The final activity of glucose oxidase in the composition is preferably 1.57 tetramethylbenzidine (TMB) megaunits per liter of composition before drying.)

Figure 2:
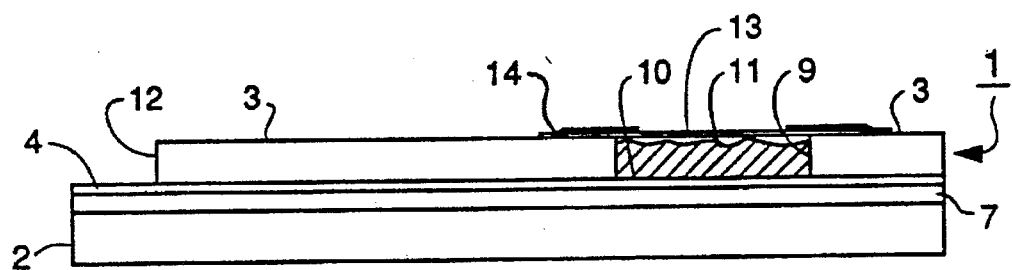
FIG. 2 is a schematic elevation of the biosensor of FIG. 1 along lines 2—2, and including the stable composition of the present invention and a cover mesh.
Figure 3:
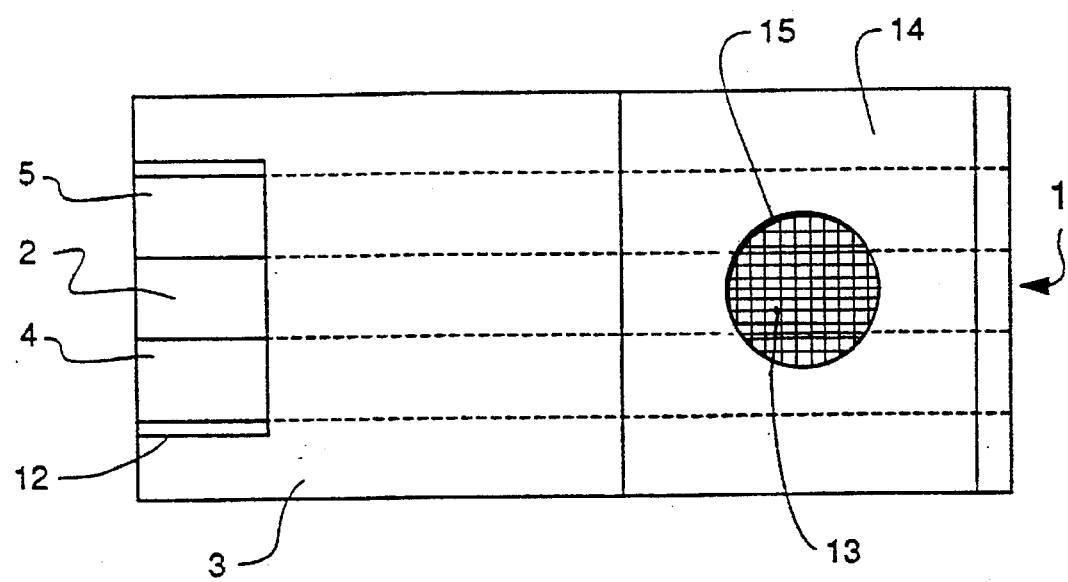
FIG. 3 is a schematic top view of the biosensor of FIG. 2.

Referring to FIGS. 1 through 3, biosensor 1 comprises first and second electrically insulating layers 2 and 3, respectively. Any useful insulating material will be suitable. Typically, plastics, such as vinyl polymers and polyimides provide the electrical and structural properties which are desired.

The biosensor shown in FIGS. 1 through 3 is intended to be mass produced from rolls of material, necessitating the selection of a material which is sufficiently flexible for roll processing and at the same time sufficiently stiff to give a useful stiffness to the finished biosensor.

Layers 2 and 3 may be of any useful thickness. In a preferred embodiment, layer 2 is about 360 microns thick and layer 3 is about 250 microns thick.

Working electrode 4 and counter electrode 5 are preferably deposited on a backing of insulator material 7, such as polyimide, to reduce the possibility of tearing the electrode before it is affixed to layer 2. Working electrode 4 and counter electrode 5 are substantially the same size and are made of the same electrically conducting material. Examples of electrically conducting materials that may be used are palladium, platinum, gold, silver, carbon, titanium, and copper. Noble metals are preferred because they provide a more constant, reproducible electrode surface area. Palladium is particularly preferred because it is one of the more difficult noble metals to oxidize and because it is a relatively inexpensive noble metal. Silver is not preferred because it is more readily oxidized by air than the other noble metals listed above. Preferably, electrodes 4 and 5 are about 0.1 micron thick and backing 7 is about 25 microns thick (commercially available from Courtalls-Andus Performance Films in California and Southwall Technologies, Inc.) (FIG. 2).

Electrodes 4 and 5 must be sufficiently separated so that the electrochemical events at one electrode do not interfere with the electrochemical events at the other electrode. The preferred distance between electrodes 4 and 5 is about 1.2 millimeters (mm).

In the preferred embodiment, electrodes 4 and 5, affixed to backing 7, are unspooled from reels and attached to layer 2 by the use of hot melt adhesive (not shown). Electrodes 4 and 5 also preferably extend from one end of layer 2 to the other end in parallel configuration. (FIG. 1)

Insulating layer 3 is fixed on top of layer 2 and electrodes 4 and 5 by the use of hot melt adhesive (not shown). Layer 3 includes cutout portion 8, which defines reagent well 9 and exposes substantially equal surface areas 10 of electrodes 4 and 5. In the preferred embodiment, cutout 8 is 4 mm by 6 mm and electrodes 4 and 5 are each 1.5 mm in width. Therefore a surface area of about 6 mm$^2$ is exposed for each of the two electrodes.

Biosensor 1 also includes a power source (not shown)in electrical connection with the working and counter electrodes and a current measuring meter (not shown) which is also in electrical connection with the working and counter electrodes.

Biosensor reagent 11 (FIG. 2) is placed in well 9 so that it covers substantially all of exposed surfaces 10 of electrodes 4 and 5 and preferably covers the exposed surface of layer 2 between the electrodes.

In the embodiment described above, which is useful for glucose determination from a fluid sample, 6 microliters (μl) of reagent 11 made by the above-stated protocol is added to well 9 formed by cutout 8. This amount of reagent 11 will substantially cover surface areas 10 on both electrodes (FIGS. 1 and 2) and will also contain a sufficient amount of reagent to perform an assay for glucose (described below).

Reagent 11 is then dried by heating at about 50° C. for about 3 minutes. Drying removes at least about 90% of the water content of the reagent, thereby resulting in a dried reagent.

After drying, a polyester or nylon mesh 13 (FIGS. 2 and 3) is preferably placed on top of the dried reagent to aid in preventing loss of reagent from the biosensor during shipping and handling and to aid in minimizing human contamination from the reagent. Mesh 13 is affixed to the biosensor by adhesive tape 14, which includes hole 15. (FIGS. 2. and 3) Hole 15 is the target area for adding a sample containing an analyte, such as glucose, to be measured by the biosensor. (FIG. 3)

After drying the reagent and affixing the mesh, the roll-formed biosensors are separated by die punching to form discrete biosensors, which are used in conjunction with a power source (i.e., a battery) in electrical connection with the working and counter electrodes and a meter for measuring electrical current.

The meter referred to above will normally be adapted to apply an algorithm to the current measurement, whereby an analyte concentration is provided and visually displayed. Improvements in such a power source and meter are the subject of commonly assigned U.S. Pat. No. 4,963,814 issued Oct. 16, 1990, U.S. Pat. No. 4,999,632, issued Mar. 12, 1991, U.S. Pat. No. 4,999,582, issued Mar. 12, 1991, and U.S. patent application Ser. No. 07/451,305 (filed Dec. 15, 1989; Notice of Allowance issued Apr. 19, 1993), the disclosures of which are hereby incorporated by reference.

For easy electrical connection of the power source and meter, additional cutout portion 12 (FIGS. 1 through 3), exposing portions of the working and counter electrodes, is preferably provided in the biosensor device.

The biosensor setup described above including the reagent, may be used in conjunction with the power source and meter to measure glucose from a fluid sample, such as a blood sample.

When a blood sample (20 microliters (μl) is sufficient) is added to reagent well 9, the reagent 11 is rehydrated, thereby solubilizing potassium ferricyanide, glucose oxidase (GOD), potassium phosphate buffer, disodium succinate and surfactant. If glucose is present in the blood sample, the following chemical reaction occurs:

An incubation period (20 seconds is sufficient) for this reaction is allowed in order to let this reaction proceed to an end point, thereby building up a significant amount of ferrocyanide. Next, a potential difference is applied (by the power source) between working and counter electrodes sufficient to cause diffusion limited electrooxidation of ferrocyanide (converting the ferrocyanide to ferricyanide) at the surface of the working electrode. (About 300 millivolts potential difference is preferred. ) The resulting diffusion limited current may be correlated to the amount of glucose in the blood sample.

The preferred reagent formulation, recited above, was optimized for both stability and performance, as reflected by good assay precision, in a glucose assay performed with the above described biosensor strip. Stability studies show that this reagent formulation will have a stability greater than 2 years. A reagent made by the protocol specified above was also stabilized when the included amount of disodium succinate hexahydrate varied from about ½ % weight/volume of reagent slurry (about 18 and ½ millimolar (mM in succinate) to about 1 and ½ % weight/volume of reagent slurry (about 55 mM in succinate). Further decreasing the amount of disodium succinate in the reagent below about 18 and ½ mM will cause further decreases in reagent stability. These further decreases in reagent stability may be described as a "tailing off" effect, wherein reagent stability decreases until there is little, if any, stability. Increasing the amount of the disodium succinate above about 55 mM in the reagent will further increase reagent stability, but only up to some upper limit where further addition of disodium succinate will not increase stability of the reagent.

The above reagent is stabilized by the inclusion of disodium succinate. Disodium succinate stabilizes both ferricyanide and glucose oxidase, thereby greatly retarding the decomposition of these reagent components and the resulting degradation of the reagent. Although the invention has been illustrated with disodium succinate, compositions that include either ferricyanide or glucose oxidase should also be stabilized by the inclusion of other succinate salts and by the inclusion of succinic acid itself. Stabilization will be observed irrespective of the reagent matrix. The reagent matrix may be an aqueous slurry, as specified in the above protocol before drying of the reagent on the biosensor strip, an aqueous solution, or a dried matrix, such as the above specified reagent after drying on the biosensor strip, or a reagent incorporated into a film, membrane, or porous matrix, such as nylon nonwoven mesh.

The present invention may be applied to a wide variety of analytical and diagnostic reagents and apparatus that include either glucose oxidase or ferricyanide or both glucose oxidase and ferricyanide. Succinic acid or a salt thereof may be included in the reagents and apparatus described in the following references, the disclosures of which are hereby incorporated by reference, as a reagent stabilizer:

Nankai et al., U.S. Pat. No. 4,431,507, issued Feb. 14, 1984;
Nankai et al., U.S. Pat. No. 5,120,420, issued Jun. 9, 1992;
Wogoman, U.S. Pat. No. 5,030,310, issued Jul. 9, 1991;
Senda et al., U.S. Pat. No. 4,820,399, issued Apr. 11, 1989;
Nankai et al., U.S. Pat. No. 4,897,173, issued Jan. 30, 1990;
Higgin et al., U.S. Pat. No. 4,545,382, issued Oct. 8, 1985;
Mindt et al., U.S. Pat. No. 3,838,033, issued Sep. 24, 1974
Nakamura et al., U.S. Pat. No. 4,224, 125, issued Sep. 23, 1980;
Hoenes et al., U.S. Pat. No. 5,122,244, issued Jun. 16, 1992;
Higgins et al., U.S. Pat. No. 4,711,245, issued Dec. 8, 1987;
Davis et al., U.S. Pat. No. 4,758,323, issued Jul. 19, 1988;
Nakamura et al., U.S. Pat. No. 4,392,933, issued Jul. 12, 1983;
McNeil et al., U.S. Pat. No. 4,830,959, issued May 16, 1989;
Phillips et al., U.S. Pat. No. 5,049,487, issued Sep. 17, 1991;
Takizawa et al., U.S. Pat. No. 4,894,137, issued Jan. 16, 1990;
Kawaguri et al., U.S. Pat. No. 5,171,689, issued Dec. 15, 1992;
Freitag, U.S. Pat. No. 4,929,545, issued May 29, 1990; and
Phillips et al., U.S. Pat. No. 5,059,394, issued Oct. 22, 1991.

(In some of these references, glucose oxidase has been cross-linked by chemical treatment (for example, by treatment with glutaraldehyde) or glucose oxidase has been covalently bound to the surface of an electrode. In such cases, the inclusion of succinic acid or a salt thereof may not additionally stabilize the reagent.)

The present invention has been disclosed in the above teachings and drawings with sufficient clarity and conciseness to enable one skilled in the art to make and use the invention, to know the best mode for carrying out the invention, and to distinguish if from other inventions and from what is old. Many variations and obvious adaptations of the invention will readily come to mind, and these are intended to be contained within the scope of the invention as claimed below.

I claim:

1. A process for stabilizing a diagnostic reagent composition comprising glucose oxidase, the process comprising the step of adding succinic acid or a salt thereof to the composition in an amount effective to stabilize the composition.

2. A process for stabilizing a diagnostic reagent composition comprising ferricyanide, the process comprising the step of adding succinic acid or a salt thereof to the composition in an amount effective to stabilize the composition.

3. A process for stabilizing a diagnostic reagent composition comprising glucose oxidase and ferricyanide, the process comprising the step of adding succinic acid or a salt thereof to the composition in an amount effective to stabilize the composition.

4. The process of claim 3, wherein the concentration of succinic acid or a salt thereof is from about 18½ millimolar to about 55 millimolar.

5. The process of claim 3, wherein the concentration of succinic acid or a salt thereof is about 37 millimolar.

6. The process of claim 4, wherein the succinic acid or a salt thereof is disodium succinate.

7. The process of claim 4, wherein the composition includes water, a dispersant and crystallization inhibitor in sufficient amount to form a slurry, and a buffer in sufficient amount to provide and maintain a pH at which glucose oxidase will catalyze the oxidation of glucose.

8. The process of claim 7, wherein the composition further includes a surfactant in sufficient amount to aid in rehydrating the composition with an aqueous sample after the slurry has been dried to form a dry reagent useful for the analysis of glucose in the sample.

9. The process of claim 8, wherein the succinic acid or a salt thereof is about 37 millimolar.

10. A diagnostic reagent composition, comprising glucose oxidase and ferricyanide in an aqueous medium, or in a dried matrix, the ferricyanide being present in an amount effective to function as a redox mediator in the catalytic oxidation of glucose; and succinic acid or a salt thereof in a concentration of about 18.5 millimolar to about 55 millimolar to stabilize the composition.

11. The composition of claim 10, further comprising:

a buffer in sufficient amount to provide and maintain a pH at which glucose oxidase will catalyze the oxidation of glucose.

12. The composition of claim 11, wherein the glucose oxidase and ferricyanide is in the dried matrix and the composition further comprises a surfactant in sufficient amount to aid in rehydrating the composition when an aqueous sample is added to the dried matrix.

13. The composition of claim 11, wherein the glucose oxidase and ferricyanide is in the aqueous medium and wherein the aqueous medium is formed by combining water and a dispersant and crystallization inhibitor.

14. The composition of claim 13, further comprising:

a surfactant in sufficient amount to aid in rehydrating the composition with an aqueous sample after the composition has been dried to form a dry reagent useful for the analysis of glucose in the aqueous sample.

15. The composition of claim 13, wherein the concentration of succinic acid or a salt thereof is about 37 millimolar.

16. The composition of claim 15, wherein disodium succinate is used to form the composition.

17. The composition of claim 14, wherein disodium succinate is used to form the composition.

18. A method for forming a stabilized rehydratable diagnostic reagent composition comprising glucose oxidase and ferricyanide, the method comprising the steps of forming an aqueous solution comprising glucose oxidase, ferricyanide in an amount sufficient to function as a redox mediator in the catalytic oxidation of glucose by the glucose oxidase, a surfactant, and succinic acid or a salt thereof in an amount sufficient to stabilize the composition, and drying the solution to remove at least about 90% by weight water to form a stabilized dry reagent composition.

19. The process of claim 18 wherein a dispersant is added to the aqueous solution to form a slurry.

20. The process of claim 18 wherein disodium succinate is used to form the aqueous solution.

* * * * *